United States Patent [19]

Palomo-Coll et al.

[11] Patent Number: 4,659,814

[45] Date of Patent: Apr. 21, 1987

[54] SALTS OF AMINO-BETA-LACTAMIC ACIDS AND PROCESS FOR THE PREPARATION THEREOF

[75] Inventors: Alberto Palomo-Coll; Juan Cabré-Castellvi; Antonio L. Palomo-Coll, all of Barcelona, Spain

[73] Assignee: Gema, S.A., Barcelona, Spain

[21] Appl. No.: 612,053

[22] Filed: May 18, 1984

[30] Foreign Application Priority Data

May 26, 1983 [ES] Spain ........................... 522728

[51] Int. Cl.$^4$ .................. C07D 205/08; C07D 471/04
[52] U.S. Cl. ..................... 540/355; 540/363; 544/279
[58] Field of Search ............. 544/279; 260/239 A, 260/239 BE; 540/355, 363

[56] References Cited

U.S. PATENT DOCUMENTS 2,865,913 12/1958 McKay ....................... 544/279
4,405,782 9/1983 Palomo-Coll ................ 544/16

FOREIGN PATENT DOCUMENTS 0048953 4/1982 European Pat. Off. ........ 260/239 A

*Primary Examiner*—Sidney Marantz
*Assistant Examiner*—Robert Benson
*Attorney, Agent, or Firm*—Scully, Scott, Murphy & Presser

[57] ABSTRACT

Amino-beta-lactamic acid salts, having the formula:

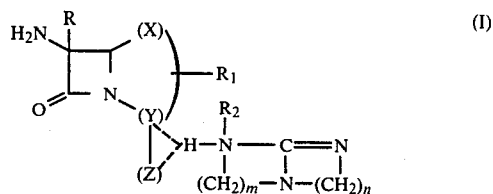

wherein: (X-Y) may form a system having from 1 to 3 carbon atoms, with or without double bond, (a) closed, in which: X is an atom selected from among carbon, oxygen, nitrogen and sulphur; Y is methylene; Z is a carboxy, sulphonic or phosphonic group (b) open, which may comprise a double bond, in which: X is an atom of hydrogen or a methyl, hydroxymethyl or thiol group, Y is an acid radical chosen from the group formed by sulphonic, phosphonic and sulphoamidic acid; Z is missing. R is an atom or hydrogen, or a methoxyl or ethoxyl group. $R_1$ is, when present, methyl, acetoxymethyl, acylthiomethyl, such as acetyl and benzoyl derivatives, methoxy, chlorine, carbamoyloxymethyl, azido, azidomethyl (alpha, beta)-thioethylamine or a thiomethyl-heterocyclic derivative of the thiazole, thiadiazole, triazole, tetrazole, oxazole, oxadiazole, pyrimidine and imidazole nuclei. $R_2$ is an atom of hydrogen or a methyl, ethyl, benzyl or phenyl group. m, n may be the same or different and may range from 1 to 4, forming a ring or m=n=O to form an open chain. A process for their preparation is also disclosed.

7 Claims, No Drawings

SALTS OF AMINO-BETA-LACTAMIC ACIDS AND PROCESS FOR THE PREPARATION THEREOF

FIELD OF THE INVENTION

The present invention relates to salts of amino-beta-lactamic acids, for application in the preparation of the N-acyl derivatives of said acids, and to a process for the preparation of said salts, of interest in the manufacture of monolactamic and bicyclic antibiotics derived from the following acids, e.g. 7-aminocephalosporanic, 7-amino-1-(oxo)-cephalosporanic, 7-amino-alpha-methoxy-desacetoxycephalosporanic, 3-amino-nocardicinic, 6-amino-2-penem-3-carboxylic, etc.

DESCRIPTION OF THE PRIOR ART

Spanish Pat. Nos. 497,076 and 504,011 disclose a process for the preparation of solutions of 7-aminocephalosporanic acids by the formation of the salts thereof with the bicyclic amidines 1,5-diazabicyclo(4,3,0)-non-5-ene (DNB) and 1,8-diazabicyclo(5,4,0)-undec-7-ene (DBU). Said patents describe the advantages obtained from the use of these salts for the preparation of cephalosporin antibiotics. Specified among these advantages are the overcoming of the particular problems of the insolubility of numerous 7-cephalosporanic acids in organic solvents, the impossibility of forming solutions with triethylamine and the difficulty of using aqueous solutions of said salts in the acylation reactions for the preparation of antibiotics of the cephalosporin group.

SUMMARY OF THE INVENTION

It has now been discovered that organic bases with the amidine function comprise the guanidine group. These are compounds with which it is possible to prepare soluble salts of a more extensive range of amino-beta-lactamic acids. Technologically, it is a great advantage to be able to have a larger number of guanidines, which may be conceived to be amino-amidines and that a pair formed by guanidine and amino-beta-lactamic acid may be easily formed to provide a solution in the chosen organic solvent.

The invention is directed towards amino-beta-lactamic acid salts, for application in the preparation of the N-aceyl-derivatives of the acids, and having the general formula:

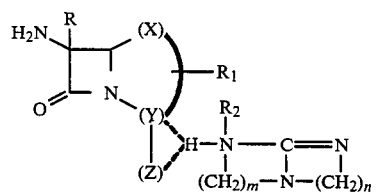

wherein:
(X-Y) may form a system having from 1 to 3 carbon atoms, with or without double bond,
(a) closed, in which
X is an atom selected from among carbon, oxygen, nitrogen and sulphur,
Y is methylene,
Z is carboxy ($CO_2$), sulphonic ($SO_3H$) or phosphonic ($PO_3H$) group.
(b) open, which may comprise a double bond, in which
X is an atom of hydrogen or a methyl, hydroxymethyl or thiol group,
Y is an acid radical chosen from the group formed by sulphonic, phosphonic or sulphoamidic acid,
Z is missing,
R is an atom of hydrogen, or a methoxy or ethoxy group,
$R_1$ is, when present, methyl, acetoxymethyl, acylthiomethyl, such as acetyl and benzoyl derivatives, methoxy, chlorine, carbamoyloxymethyl, azido, azidomethyl (alpha, beta)-thioethylamine or a thiomethyl-heterocyclic derivative of the thiazole, thiadiazole, triazole, tetrazole, oxazole, oxadiazole, pyrimidine and imidazole nuclei,
$R_2$ is an atom of hydrogen or a methyl, ethyl, benzyl or phenyl group,
m, n may be the same or different and may range from 1 to 4, forming a ring or $m=n=0$ to form an open chain.

When $R_2$ is hydrogen and $m=n=3$ in formula I, the resulting compound has the formula:

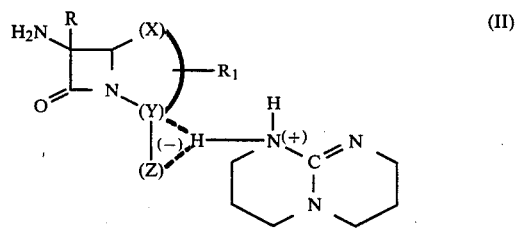

When $R_2$ is $-CH_3$, $m=n=0$ and $-(CH_2)_m=$two methyl groups and $-(CH_2)_n=$one methyl group and an atom of hydrogen in formula I, the resulting compound has the formula:

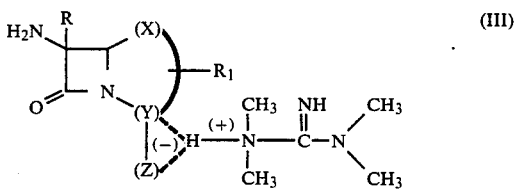

When $X=-CH_3$, $Y=-SO_3^-$, $R=-H$, $R_2=-CH_3$, $m=n=3$ and Z and $R_1$ are missing, in formula I, the resulting compound has the formula:

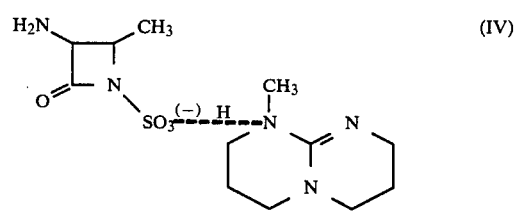

When $X=-S-$, $(X-Y)=CH_2-C=C-$, $Z=-COO^-$, $R=-H$,

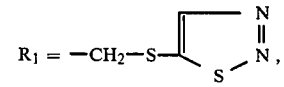

$R_2$=—$CH_3$, m=n=0 and —$(CH_2)_m$— and —$(CH_2)_n$— are two methyl groups, in formula I, the resulting compound has the formula:

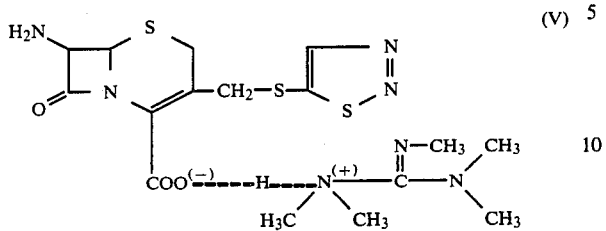

When X=—S—, (X-Y)=—$CH_2$—C=C<, X=—$COO^-$, R=—H,

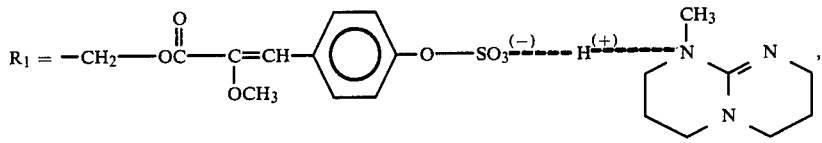

$R_2$=—$CH_3$, m=n=0 and —$(CH_2)_m$=two methyl groups and —$(CH_2)_n$=one methyl group and one atom of hydrogen, in the formula I, the resulting compound has the formula

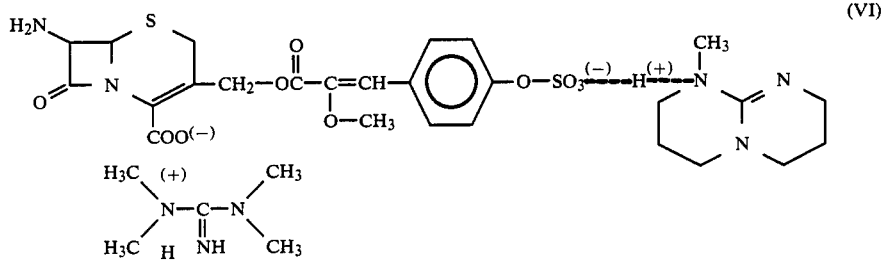

When X=—H, Y=—$PO_3H^-$, Z=0, R=—H, $R_1$=0, $R_2$=—$CH_3$ and m=n=0, and —$(CH_2)_m$— and —$(CH_2)_n$—=two methyl groups, in formula I, the resulting compound has the formula:

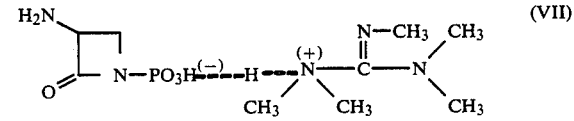

A further object of the invention is to provide a process for the preparation of the said salts, in which a compound having the formula:

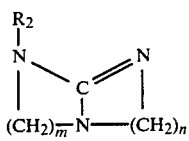

in which X, Y, (X-Y), Z, R and $R_1$ are as defined hereinbefore, is reacted in a solvent, at a temperature of from −50° to +25° C. with the stoichiometric amount of a compound of the formula in which $R_2$, m and n are as defined hereinbefore to prepare a solution of a salt of a compound of formula I.

For the purposes of the invention, a sulphonamide, because of its acid properties, is deemed to be an acid component, included within the terminology used herein.

As stated above, the Formula VIII compounds may comprise a double bond or a conjugated system and the (X-Y) chain may be formed by one to three carbon atoms. An example of a double bond is 6-amino-pen-2-em-3-carboxylic acid and the 2-methyl derivative thereof. When there are no links between (X) and (Y), the Formula VIII compounds comprise the monolactams, such as the 3-amino-nocardicinic acids and the monolactamic acids, the latter forming the known derivatives of 3-amino-4-oxo-azetidinin-1-sulphonic acid.

In the case of the bicyclic guanidines of Formula IX, as stated above, m may be the same as or different from n, preferably between 2 and 4.

For the linear guanidines m=n=0, the nitrogen atoms may be substituted by methyls, ethyls, benzyls or aryls, preferably methyls and ethyls. Representative compounds are tetramethylguanidine, pentamethylguanidine, tetraethylguanidine, tetramethylethyguanidine, tetramethylbenzylguanidine and methylarylguanidines, all of them of commercial use or easily prepared by known processes described in the scientific and technical literature (P. Molina et al; Synthetic Communications, 13, 67, 1983). Preferred bicyclic guanidines are 1,5,7-triazabicyclo-(4,4,0)-dec-5-ene, the 7-methyl, 7-ethyl, 7-benzyl and 7-phenyl derivatives thereof, all described in the Examples hereof, respectively, with the initials TDB, M-TDB, E-TDB, B-TDB and P-TDB, for better understanding.

Technically the guanidines may be conceived to be amino-amidines, with the amino group specifically supported on the aminic carbon atom. The simplest term is guanidine, wherein, in the general formula IX, $R_2$, $(CH_2)_m$ and $(CH_2)_n$ are hydrogen atoms. The simplest term of a monocyclic guanidine is the Formula IX compound, the term $(CH_2)_m$ or, otherwise the term $(CH_2)_n$ being a ring for n which may vary from two to four, the other term being a straight chain or open. In other words, in the latter case m would be 0, as for example, in N,N'-trimethyl-N,N''-propyleneguanidine, which has the following formula

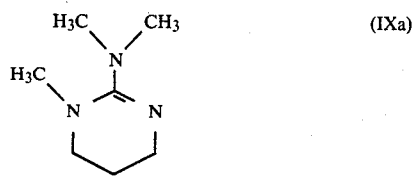
(IXa)

The salt of the Formula I compounds will comprise (Y) or (Z) as acid groups, depending on the meaning given hereinabove. Thus soluble salts of straight chain guanidines and of bicyclic guanidines are formed with the beta-lactam nuclei, all of interest in the preparation of antibiotics which result from the subsequent N-acylation reaction.

For practical purposes, in the preparation of solutions, the corresponding compound having the beta-lactam nucleus of Formula VIII is suspended in the chosen solvent. A formula IX guanidine is added gradually with good stirring at a temperature of 5° C. or at room temperature, for example, until the solution of VIII in the form of a general Formula I salt is just attained. The amount of IX to be used is determined essentially by the stoichimetry of the reaction, generally 1:1, depending on the previously analytically determined purity of the products.

To the thus prepared solution, containing a Formula I compound, there is added the acylating reactant, following the usual processes of using activated carboxylic acids, such as acid chlorides, anhydrides, mixed anhydrides, active esters or systems formed by the carboxylic acid and activation reactants such as the carbodiimides and phosphorus compounds such as the phosphoramide hydrochlorides and the phosphorus hydrochlorides. All of these are known and described in the scientific and technical literature.

Solvents such as dichloromethane, 1,2-dichloroethane, chloroform, dimethylacetamide, dimethylformamide, acetonitrile, methanol and the binary or ternary mixtures thereof, in which acetone, methylethylketone, 1,4-dioxane, tetrahydrofuran and methyltert-butyl ether may be incorporated, are appropriate for the formation of Formula I compounds.

Numerous advantages are provided by the process of using the Formula I compounds for the preparation of antibiotics derived from VIII. Exemplary advantages may be:

(1) the use of organic bases derived from guanidine and bicyclic guanidines which are available on the market at low cost.
(2) a wider range of bases from which to select the most appropriate for the purposes of the invention is available.
(3) the process of recovery of the bases and organic solvents is extremely simple and cheap.
(4) there is no need to apply a strict control of absence of humidity or the use of an inert atmosphere for the preparation of the Formula I compounds.
(5) there is no limitation for the use of active forms of the carboxylic acids.

(6) a wide range of solvents and temperatures may be selected for the acylation reaction of Formula I products.
(7) solutions of Formula I compounds may be prepared from Formula VIII compounds of high purity. This allows antibiotics biologically and chemically conforming to the highest analytical requirements to be obtained.
(8) in general, excellent antibiotic yields are obtained, in view of the wider available range of organic bases for the formation of the Formula I compound, of the acylation reaction solvent and of the precipitation and isolation solvent.
(9) all the foregoing properties are the basis for the manufacture of the beta-lactam antibiotics using a new, improved technology.
(10) no secondary or racemisation, epimerisation or isomerisation reactions, which would cause loss of biological activity of the antibiotic prepared, are produced.

The Formula I compounds are solid hygroscopic salts which may be isolated from the solutions thereof by evaporation of the solvent. It is not easy to determine the melting point thereof with any precision, since they soften at temperatures close to room temperature. In general they are characterised by giving, in infra red spectrum, absorbancies at 1740-1755 (beta-lactam) and 1600-1605 (COO−) and signals at 3.03 ppm (CH₃; TMG), among others, in the proton magnetic resonance spectrum. Aqueous solutions or organic solvents such as dimethylsulphoxide are useful for determining the optical activity. The results obtained by distillation of the organic solvent and immediate redissolution are given in some of the Examples.

It was possible to determine the optical activities of the salts under these conditions. Examples of the $[\alpha]_D^{20}$ value for the tetramethylguanidine salts of the following acids are: 7-aminodesacetoxycephalosporanic = +76.7 (1% dimethylsulphoxide) and +83.6 (1% water); 7aminocephalosporanic acid = +60.3 (1% dimethylsulphoxide) and +88.7 (1% water); 7-amino-3-azidomethyl-3-cephem-4-carboxylic acid = +50.9 (1% dimethylsulphoxide) and +44.7 (1% water) and 7-amino-3-(5-methyl-1,3,4-thiadiazol-2-yl-thiomethyl)-3-cephem-4-carboxylic acid = −70.4 (1% dimethylsulphoxide) and −57.2 (1% water).

The following Examples are provided to provide a better illustration of the invention.

EXAMPLE 1

Salt of 7-amino-3-(1-methyl-1,2,3,4-tetrazol-5-yl-thio-methyl)-3-cephem-4-carboxylic acid.

1.3 g of tetramethylguanidine (TMG) were added to a suspension of 3.28 g of the acid of the title in 50 ml of dichloromethane, cooled to −10° C. A solution was instantly formed. One equivalent of triethylamine 2-ethylhexanote was added to the above solution, with no precipitate being formed.

EXAMPLE 2

The previous Example was followed, but the dichloromethane was replaced by 30 ml of methanol, to give a solution. The addition of triethylamine pivalate did not cause any precipitation.

EXAMPLE 3

Example 1 was followed, but the dichloromethane was replaced by 30 ml of acetonitrile and the tetramethyl-guanidine by 1.4 g of pentamethylguanidine, to give a solution. The addition of triethylamine pivalate did not cause any precipitation.

EXAMPLE 4

Example 1 was followed, but the dichloromethane was replaced by 40 ml of 1,2-dichloroethane and the tetramethyl-guanidine by 1.9 g of tetramethyl-2-ethyl-guanidine, to give a solution. The addition of triethylamine 2-ethylhexanoate or triethylamine pivalate did not cause any precipitation.

EXAMPLE 5

Salt of 7-amino-3-[(2-amino-1,3,4-thiadiazol-5-yl)thiomethyl]-3-cephem-4-carboxylic acid 2.2 g of tetramethyl-2-benzylguanidine were added, with stirring, to a suspension of 3.45 g of the acid of the title in 20 ml of methanol, cooled to −10° C. A solution was formed in about 10 minutes and was adjusted with a few drops of tetramethyl-2-benzylguanidine, as required. The addition of triethylamine pivalate caused no precipitation.

EXAMPLE 6

Example 5 was followed, but the methanol was replaced by 40 ml of 1,2-dichloroethane plus 8 ml of methanol, to give a solution.

EXAMPLE 7

Example 5 was followed, but the methanol was replaced by a mixture of 40 ml of dichloromethane and 8 ml of methanol, to give a solution. The addition of triethylamine pivalate did not cause any precipitation.

EXAMPLE 8

Salt of 7-amino-3-azidomethyl-3-cephem-4-carboxylic acid 1.2 g of tetramethylguanidine were added to a suspension of 2.51 g of the acid of the title in 20 ml of dichloromethane, cooled to −10° C. The solution was adjusted with more base, depending on the purity thereof. A solution was formed in a short time and the corresponding salt was obtained in the form of an oil by evaporation of the solvent at reduced pressure. The oil was suspended in ethyl ether and isolated by filtration as a very hygroscopic solid which was dried under vacuum at room temperature. IR(KBr)$\nu$max. cm$^{-1}$: 1755 (C=O, $\beta$-lactam), 1602 (COO$^-$), 2095 and 2025 (—N$_3$). $^1$H-NMR (CDCl$_3$)$\delta$ppm: 3.03 (CH$_3$, TMG). $[\alpha]_D^{20}$=+50,9° (C=1% dimethylsulphoxide-DMSO $[\alpha]_D^{20}$=+44.7° (C=1% H$_2$O).

EXAMPLE 9

Example 8 was followed, but the dichloromethane was replaced by 1,2-dichloroethane and a solution was formed.

EXAMPLE 10

Example 8 was followed, but the dichloromethane was replaced by acetonitrile and a solution was formed.

EXAMPLE 11

Example 8 was followed, but the dichloromethane was replaced by dimethylacetamide and a solution was formed.

EXAMPLE 12

Example 8 was followed, but the dichloromethane was replaced by dimethylformamide and the tetramethylguanidine by 1.5 g of tetramethyl-2-ethylguanidine and a solution was formed.

EXAMPLE 13

Example 8 was followed, but the dichloromethane was replaced by nitromethane and a solution was formed.

EXAMPLE 14

Example 8 was followed, but the dichloromethane was replaced by chloroform and a solution was formed.

EXAMPLE 15

Salt of 7-amino-3-(1-phenyl-tetrazol-2-yl-thiomethyl)-3-cephem-4-carboxylic acid 1.4 g of pentamethylguanidine were added to a suspension of 3.90 g of the acid of the title in 20 ml of dichloromethane, cooled to −10° C. The solution was adjusted in accordance with the purity of the base. A solution was formed instantly. The addition of triethylamine 2-ethylhexanoate caused no precipitation.

EXAMPLE 16

Example 15 was followed, but the dichloromethane was replaced by 40 ml of acetonitrile and the pentamethyl guanidine by 1.2 of tetramethylguanidine and a solution was formed. The addition of triethylamine pivalate caused no precipitation.

EXAMPLE 17

Salt of 7-amino-3-azidomethyl-3-cephem-4-carboxylic acid 1.46 of tetramethyl-2-ethylguanidine were added to a suspension of 2.54 g of the acid of the title in 20 ml of isopropanol, followed by adjustment depending on the purity of the base. A solution was formed in a short time and no precipitation was caused by the addition of triethylamine pivalate.

EXAMPLE 18

Salt of 7-amino-3-acetoxymethyl-3-cephem-4-carboxylic acid 5.8 g of tetramethylguanidine were added to a suspension of 13.6 g of the acid of the title in 100 ml of isopropanol, followed by adjustment depending on the purity of the base. A solution was formed after about 15 minutes stirring.

EXAMPLE 19

Salt of 7-amino-3-(5-methyl-1,3,4-thiadiazol-2-yl-thiomethyl)-3-cephem-4-carboxylic acid 16.5 g of tetramethyl-2-benzylguanidine were added to a suspension of 17.2 g of the acid of the title in 100 ml of methanol at −20° C. A solution was formed instantaneously.

EXAMPLE 20

Salt of 7-amino-3-(1,2,3-triazol-5-yl-thiomethyl)-3-cephem-4-carboxylic acid 1.2 of tetramethylguanidine were added to a suspension of 3.13 g of the acid of the title in 30 ml of dichloromethane at −15° C. A solution was formed. One equivalent of triethylamine pivalate was added, with no precipitate being formed.

EXAMPLE 21

Salt 7-amino-3-(1,3,4-thiadiazol-2-yl-thiomethyl)-3-cephem-4-carboxylic acid 1.45 g of tetramethyl-2-ethylguanidine were added to a suspension of 3.30 g of the acid of the title in 30 ml of 1,2-dichloroethane, followed by adjustment depending on the purity of the base. After stirring for a short time at −5° C. a solution was formed. One equivalent of the triethylamine salt of isononanoic acid was added, with no precipitate being formed.

EXAMPLE 22

Salt of 7-amino-3-acetyl-thiomethyl-3-cephem-4-carboxylic acid 2.2 g of tetramethyl-2-benzylguanidine were added to a suspension of 2.88 g of the acid of the title in 30 ml of dichloromethane at −10° C., followed by adjustment depending on the purity of the base. After stirring for a short time a solution was formed. One equivalent of the triethylamine salt of pivalic acid was added, with no precipitate being formed.

EXAMPLE 23

Example 22 was followed, but the acid of the title was replaced by the corresponding equivalent of the 3-phenylthiomethyl derivative, to give a solution. The addition of triethylamine pivalate caused no precipitation.

EXAMPLE 24

Salt of 7-beta-amino-7-alpha-methoxy-3-acetoxymethyl-3-cephem-4-carboxylic acid 1.2 g of tetramethylguanidine were added to a suspension of 3.02 g of the acid of the title in 30 ml of chloroform at −10° C., followed by adjustment depending on the purity of the base. After a short time a solution was formed, One equivalent of triethylamine pivalate was added, with no precipitate being formed.

EXAMPLE 25

Salt of 7-amino-3-(5-methyl-1,3,4-thiadiazol-2-yl)-3-cephem-4-carboxylic acid 1.2 g of tetramethylguanidine were added to a suspension of 2.98 g of the acid of the title in 35 ml of dichloromethane at −10° C., followed by adjustment depending on the purity of the base. After a short time a solution was formed. One equivalent of N-ethylpiperdine 2-ethylhexanoate was added, with no precipitate being formed.

EXAMPLE 26

Salt of 7-amino-3-(1-H-5-methyl-1,3,4-triazol-2-yl)-3-cephem-4-carboxylic acid 1.3 g of pentamethylguanidine were added to a suspension of 2.81 g of the acid of the title in 30 ml of dichloromethane at −5° C., followed by adjustment depending on the purity of the base. After a short time a solution was formed. N-methylmorpholine isononanoate was added, with no precipitate being formed.

EXAMPLE 27

Salt of 7-amino-3-(phenyl-thiomethyl)-3-cephem-4-carboxylic acid

One equivalent of amidine, tetramethylbenzylguanidine, tetramethyl-2-ethylguanidine or other similar compound were added to a suspension of 3.23 g of the acid of the title in 25 ml of dichloromethane at −10° C. The amount of base was adjusted depending on the purity thereof and after a short period of stirring a solution of the corresponding salt was obtained.

EXAMPLE 28

Example 27 was followed and the dichloromethane was replaced by chloroform. A solution of the corresponding salt was obtained.

EXAMPLE 29

Salt of 7-amino-3-gamma-pyridyl-thiomethyl)-3-cephem-4-carboxylic acid

One equivalent of amidine, tetramethylguanidine, pentamethylguanidine, tetramethyl-2-benzylguanidine or other similar compound were added to a suspension of 3.24 g of the acid of the title in 30 ml of acetonitrile at −10° C. The amount of base was adjusted and a solution of the corresponding salt was obtained.

EXAMPLE 30

Salt of 7-amino-3-(1,3-thiazolin-2-yl)thiomethyl-3-cephem-4-carboxylic acid 1.2 g of tetramethylguanidine were added to a suspension of 3.31 g of the acid of the title in 50 ml of methylene chloride, to give a solution of the corresponding salt.

EXAMPLE 31

Salt of 7-amino-3-(3-methylisoxazol-5-yl)carbonylthio-methyl-3-cephem-4-carboxylic acid 1.5 of tetramethyl-2-ethylguanidine were added to a suspension of 3.55 g of the acid of the title in 10 ml of dimethylacetamide, to give a solution of the corresponding salt.

EXAMPLE 32

Salt of 7-amino-3-(methylcarbonyl-thiomethyl)-3-cephem-4-carboxylic acid 2.1 g of tetramethyl-2-benzylguanidine were added to a suspension of 2.88 g of the acid of the title in 25 ml of methylene chloride, to give a solution of the corresponding salt.

EXAMPLE 33

Salt of 7-beta-amino-7-alpha-methoxy-3-(methylcarbonyl-thiomethyl)-3-cephem-4-carboxylic acid 1.3 g of pentamethylguanidine were added to a suspension of 3.18 g of the acid of the title in 10 ml of dimethylacetamide, to give a solution of the corresponding salt.

EXAMPLE 34

Salt of 7-amino-3-(methoxymethyl-carbonyl-thiomethyl)-3-cephem-4-carboxylic acid 2.05 g of tetramethyl-2-benzylguanidine were added to a suspension of 3.2 g of the acid of the title in 10 ml of methanol, to give a solution of the corresponding salt.

EXAMPLE 35

Salt of 7-amino-3-(3-methoxy-pyridazine-6-yl)thiomethyl-3-cephem-4-carboxylic acid 1.2 g of tetramethylguanidine were added to a suspension of 3.54 g of the acid of the title in 25 ml of isopropanol and 25 ml of methanol, to give a solution of the corresponding salt.

EXAMPLE 36

Salt of 7-beta-amino-7-alpha-methoxy-3-(1-methyl-1,2,3,4-tetrazol-5-yl)thiomethyl-3-cephem-4-carboxylic acid 1.2 g of tetramethylguanidine were added to a suspension of 3.58 g of the acid of the title in 25 ml of methylene chloride, to give a solution of the corresponding salt.

EXAMPLE 37

Salt of 7-beta-amino-7-alpha-methoxy-3-desacetoxy-3-cephem-4-carboxylic acid 1.2 g of tetramethylguanidine were added to a suspension of 2.44 g of the acid of the title in 50 ml of methylene chloride, to give a solution of the corresponding salt.

EXAMPLE 38

Salt of 7-amino-3-chloro-3-cephem-4-carboxylic acid 1.35 g of pentamethylguanidine were added to a suspension of 2.34 g of the acid of the title in 50 ml of chloroform, to give a solution of the corresponding salt.

EXAMPLE 39

Salt of 7-amino-3-(1-carbonyl-methyl-1,2,3,4-tetrazol-5-yl-thiomethyl)-3-cephem-4-carboxylic acid 1.5 g of tetramethyl-2-ethylguanidine were added to a suspension of 3.7 g of the acid of the title in 15 ml of dimethylacetamide, to give a solution of the corresponding salt.

EXAMPLE 40

2-oxo-3-amino-3-methoxy-azetidine-1-sulphonic acid tetramethylguanidine salt 1.2 g of tetramethylguanidine were added to a suspension of 1.65 g of monolactamic acid of the title in 10 ml of dimethylacetamide, to give a solution of the salt of the title.

EXAMPLE 41

When the tetramethylguanidine of the previous Example was replaced by 1.5 g of tetramethyl-2-ethylguanidine, a solution of the corresponding salt was obtained.

EXAMPLE 42

2-oxo-3-amino-3-methoxy-azetidine-1-sulphonic acid tetramethylguanidine salt 1.2 g of tetramethylguanidine were added to 1.96 g of monolactamic acid in 10 ml of acetonitrile to give a solution of the compound of the title.

EXAMPLE 43

When the tetramethylguanidine of the previous Example was replaced by 1.35 g of pentamethylguanidine, a solution of the corresponding salt was obtained.

EXAMPLE 44

2-oxo-3-amino-3-methoxy-4-methyl-azetidine-1-sulphonic acid tetramethylguanidine salt 1.2 g of tetramethylguanidine was added to 2.1 g of monolactamic acid in 5 ml of dimethylacetamide and 10 ml of methylene chloride to give a solution of the compound of the title. When the tetramethylguanidine was replaced by the equivalent of pentamethylguanidine, tetramethyl-2-ethylguanidine and tetramethyl-2-benzylguanidine, solutions of the corresponding salts were obtained.

EXAMPLE 45

2-oxo-3-amino-3-methoxy-4-methyl-azetidine-1-sulphonic acid tetramethylguanidine salt 1.2 g of tetramethylguanidine were added to 2.09 g of monolactamic acid in 10 ml of dimethylformamide. A solution was formed with stirring.

EXAMPLE 46

When the dimethylformamide and the base of the previous Example were replaced by dimethylacetamide and pentamethylguanidine respectively, a solution was obtained.

EXAMPLE 47

When the dimethylacetamide and the base of the previous Example were replaced by acetonitrile and tetramethyl-2-ethylguanidine, respectively, a solution of the corresponding salt was obtained.

EXAMPLE 48

2-oxo-3-amino-3-methoxy-4-methyl-azetidine-1-N-methyl sulphonic acid pentamethylguanidine salt 1.3 g of pentamethylguanidine were added to 2.23 g of monolactamic acid in 5 ml of methylene chloride and 10 ml of dimethylformamide to give a solution.

EXAMPLE 49

When the solvent and the base of the previous Example were replaced by 10 ml of methylene chloride, 10 ml of dimethylacetamide and the equivalent of tetramethylguanidine, tetramethyl-2-ethylguanidine or tetramethyl-2-benzylguanidine, respectively, solutions of the corresponding salts were also obtained.

EXAMPLE 50

Alpha(3-amino-2-oxo-1-azetidinin)-gamma-(thioacetyl)butenoic acid P-TDB salt 2.3 g of P-TDB were added to a mixture of 2.44 g of the alpha(3-amino-2-oxo-1-azetidinin)-gamma-(thioacetyl)butenoic acid in 25 ml of dichloromethane and a solution was obtained with stirring.

EXAMPLE 51

Alpha(3-amino-2-oxo-1-azetidinin)-gamma-(thioacetyl)butenoic acid TDB salt

When the P-TDB of the previous Example was replaced by 1.45 g of TDB a solution of the acid was immediately obtained.

EXAMPLE 52

Alpha-(3-amino-2-oxo-1-azetidinin)-gamma-(2-mercapto-5-methyl-1,3,4-thiadiazole)butenoic acid M-TDB salt 1.54 g of M-TDB were added to a mixture of 3.00 g of alpha-(3-amino-2-oxo-1-azetidinin)-gamma-(2-mercapto-5-methyl-1,3,4-thiadiazole)butenoic acid in 25 ml of dichloromethane and a solution was obtained.

EXAMPLE 53

Alpha-(3-amino-2-oxo-1-azetidinin)-gamma-(2-mercapto-5-methyl-1,3,4-thiadiazole)butenoic acid TDB salt When the M-TDB and the dichloromethane of the previous Example was replaced by 1.40 g of TDB and 20 ml of methanol, respectively, a solution was also obtained.

EXAMPLE 54

3-amino-nocardicinic acid B-TDB salt 2.30 g of B-TDB were added to a suspension of 1.83 g of 3-amino-nocardicinic acid in 20 ml dichloromethane. A solution was obtained by stirring at room temperature.

EXAMPLE 55

6-amino-3-methyl-carbapenem-3-carboxylic acid E-TDB salt 1.67 g of E-TDB were added to a mixture of 1.83 g of 6-amino-3-methyl-carbapenem-3-carboxylic acid in 25 ml of dichloromethane, a total solution being obtained in a few minutes.

EXAMPLE 56

6-amino-3-methyl-carbapenem-3-carboxylic acid E-TDB salt

When the dichloromethane of the previous Example was replaced by 25 ml of dimethylacetamide, the same result was obtained.

EXAMPLE 57

Thienamycin TDB salt 1.40 g of TDB were added to a suspension of 2.74 g of thienamycin in 20 ml of acetonitrile with stirring at room temperature to give a solution.

EXAMPLE 58

7-alpha-amino-3-[(1,2,3-thiadiazol-5-yl)thiomethyl]-3-cephem-4-carboxylic acid tetramethylguanidine salt 1.15 g of tetramethylguanidine were added to a suspension of 3.32 g of 7-alpha-amino-3-[(1,2,3-thiadiazol-5-yl)thiomethyl]-3-cefem-4-carboxylic acid in 25 ml of dichloromethane. A solution was obtained by stirring at room temperature.

EXAMPLE 59

7-amino-3-[(1,2,3-thiadiazol-5-yl)thiomethyl]-3-oxacephem-4-carboxylic acid tetramethylguanidine salt Following the previous Example, but using 3.16 g of 7-amino-3-[(1,2,3-thiadiazol-5-yl)thiomethyl]-3-oxacephem-4-carboxylic acid a solution was also obtained.

EXAMPLE 60

7-beta-amino-7-alpha-methoxy-3-[(1,2,3-thiadiazol-5-yl)thiomethyl]-3-cephem-4-carboxylic acid tetramethylguanidine salt Following Example 58 but using 3.62 g of 7-beta-amino-7-alpha-methoxy-3-[(1,2,3-thiadiazol-5-yl)thiomethyl]-3-cephem-4-carboxylic acid a solution was obtained under the same conditions.

EXAMPLE 61

7-(D-alpha-amino phenylacetamido)desacetoxycephalosporanic acid (cephalexin)

0.266 g of gamma-picoline hydrochloride (or the corresponding amount of pyridine or beta-picoline) was added to 10.96 g of potassium N-(1-ethoxycarbonylpropen-2-yl)-alpha-aminophenylacetate in 40 ml of methylene chloride, followed by 0.8 g of N-methylacetamide. The mass was cooled to −35°/−40° C. and 4.22 g of 100% pivaloyl chloride were added, the mass was held at −35°/−38° C. for 15 minutes and thereafter a solution, precooled to −15°/−20° C., of 6.45 g of 7-amino-desacetoxycephalosporanic acid (7-ADCA) in 50 ml of methylene chloride and 3.49 g of tetramethylguanidine were added over 20 minutes. The temperature of the reaction mass was held at −55°/−50° C. during the addition and was allowed to react at −38°/−40° C. for 5 hours. Thereafter 0.42 ml of diethylamine was added to destroy the excess anhydride, the mixture was stirred at −35°/−40° C. for 15 minutes and thereafter a mixture of 27 ml of water and 6 ml of 37.5% hydrochloric acid was added. The temperature of the mass was −12° C. and was allowed to rise to 0° C. in about 10 minutes. The pH was 0.92-1 and was adjusted to 0.20-34 over 10 minutes and was held at this value for 20 minutes. The total consumption of hydrochloric acid was 7.7 ml, with the temperature being held at 0° C.

The mixture was decanted and 5 ml of water and 40 ml of acetonitrile were added to the aqueous phase. Precipitation was caused by adding triethylamine to raise the pH to 3-3.1 at 25° C., with heating for 6 minutes to 40° C. A rapid precipitation and pH change to 2.5-2.6 was observed. The slow addition of the base was continued at 40°-41° C. over 45 minutes to pH 5.45-5.5. The amount of base consumed was 8.25 ml. The mixture was stirred for 30 minutes at 40° C., was filtered, was washed with a mixture of acetonitrile-water (48-12 ml) and acetonitrile (60 ml) and dried to give 9.70 g of cephalexin with 5% moisture (isolation yield 88.2%), cephalexin/ADCA ratio 1:1.51, microbiological purity 99-100%.

An identical yield was obtained at an isoelectric pH of 5 to 5.1 when the triethylamine was replaced by ammonium hydroxide in the precipitation.

A similar yield was obtained in the formation of the mixed anhydride when replacing the methylene chloride by 30 ml of acetonitrile and the 50 ml of methylene chloride in the 7-ADCA solution by 30 ml of acetonitrile and hydrolysing with the same amount of water at pH 0.4-0.5 and precipitating as described in Example 62.

EXAMPLE 62

7-D-2-amino-2-(1,4-cyclohexadienyl)acetamido-cephalosporanic acid (cephradine)

9.89 g of sodium N-(1-methoxycarbonylpropen-2-yl)-alpha-amino-1,4-cyclohexadienyl-phenylacetate in 27 ml of methylene chloride were cooled to −25°/−30° C. and 0.8 g of N-methylacetamide and 0.0722 g of pyridine hydrochloride or the corresponding salt of beta- or gamma-picoline were added, the mixture was stirred for 2 minutes and 4.22 g of 100% pivaloyl chloride were added. The temperature was raised to −16° C. and was held at between −13°/−15° C. for half an hour. It was then cooled to −50° C. A solution of 6.45 g of 7-ADCA, 50 ml of methylene chloride and 3.49 g of tetramethylguanidine was cooled to −10°/−15° C. and was then added over a period of 5 minutes to the above mixture at a temperature of between −50° and −55° C. The funnel of the 7-ADCA solution was washed with 4 ml of methylene cloride which were added to the reaction mass. The mixture was allowed to react for 8 hours at −38°/−39° C., followed by the addition of 0.47 ml of diethylamine. The mixture was stirred for 15 minutes at −35°/−40° C. and a solution, precooled to 0°/+5° C., of 25 ml of water and 6 ml of 37.5% hydrochloric acid was added. The temperature was allowed to rise to 0° C. in 5 minutes, the pH being 0.68. The mixture was stirred for 5 minutes and the pH was adjusted to 0.24 over a further 5 minutes and was then held for 20 minutes at 0° C. and pH 0.2. The total hydrochloric acid consumption was 7.3 ml.

The system comprises three phases, the methylene chloride was decanted off and the intermediate phase and the aqueous phase was combined, the funnel being washed with 4 ml of water. 40 ml of acetonitrile were added, the pH being 0.33. Precipitation was caused at −20°/−21° C. by addition of 3.55 ml of triethylamine (TEA) to pH 3, at which the precipitation starts. The pH varied over 20 minutes to 2.29. Addition of triethylamine was continued over 35 minutes to pH 5.44, with a total TEA consumption of 7.025 ml.

The mixture was stirred for 10 minutes at 20° C. and was cooled to 0°/+5° C. over a further 10 minutes, was stirred for 30 minutes and the pH at 0° C. was 5.58 to 5.6. The mixture was filtered, washed with 80% acetonitrile and finally with 100% acetonitrile (33.5 ml) to give 10.42 g of the antibiotic, with 6% water of crystallisation. The cephradine/7-ADCA ratio was 1:1.62 and the microbiological purity was 99-100%. When the triethylamine was replaced by ammonium hydroxide in the precipitation, an identical yield was given at the isoelectric pH of 5 to 5.1.

An identical result was obtained when 40 ml of acetonitrile was replaced by 75 ml of isopropanol in the precipitation stage, with a final pH of 5.4-5.5.

EXAMPLE 63

7-(1(1H)-tetrazolylacetamido)-3-2-(5-methyl-1,3,4-thiadiazolyl)thiomethyl-3-cephem-4-carboxylic acid (cephazolin)

4.9 g of tetramethylguanidine were added to a suspension of 10.75 g of technically pure 7-amino-3-(5-methyl-1,3,4-thiadiazol-2-yl-thiomethyl)-3-cephem-4-carboxylic acid in 150 ml of dichloromethane, at a temperature of −10° C. A solution was immediately formed. To this solution there was added triethylamine pivalate, prepared with 1.5 g of pivalic acid and 4.0 ml of triethylamine. Thereafter 9.5 g of tetrazolylacetic anhydride were added at one go. The solution was stirred for 90 minutes at a temperature of 15° C. and 325 ml of water and a few drops of sodium dioctylsulphosuccinate solution were added. The mixture had a pH of 3.5 at 20° C., varied to pH 3.8 in one minute and dropped to pH 3.62 after about 15 minutes (22° C.). The small amount of grey precipitate was isolated (0.05 g). The aqueous phase was decanted off, was decoloured with 2.5 g of activated carbon for 15 minutes, the pH being 4.48. It was filtered (a 0.025 g portion of product was isolated from the carbon with an aqueous triethylamine solution. 250 ml of methylisobutylketone were added to the aqueous liquors and the pH gradually rose to 3.0 (23° C.), 1 g of a yellowish product being separated out. The pH of the decanted colourless liquors was adjusted to 1.04 slowly (115 minutes) with the addition of 1N hydrochloric acid. The precipitation started previously to this at pH 2.98. After cooling to 0°/+5° C., the mixture was filtered, washed with water and dried at reduced pressure. 12.00 g of the compound of the title were obtained, with a 98/99% analytical purity and a microbiological activity of 98-100% in comparison with a standard. A further amount of the compound of the title was isolated, by purification from the 1.5 g of crude product, with an overall yield of 92% of theory.

EXAMPLE 64

7[(6,7-dihydroxy-4-oxo-4H-1-benzopyran-3-carboxyamido)-2-(4-hydroxyphenylacetamido)]-3[(1-carboxymethyl-1H-tetrazol-5-yl)thiomethyl-3-cephem-4-carboxylic]acid 0.5 g of pyridine hydrochloride or of the corresponding hydrobromide were added to 7.9 g of potassium 6,7-dihydroxy-4-oxo-4H-1-benzopyran-3-carboxyamido-D(-)alpha-4-hydroxyphenyl acetate in 75 ml of methylene chloride. The mixture was cooled to −20°/−25° C. and 2.29 g of 100% pivaloyl chloride were added, followed by stirring for 45 minutes to 60 minutes at −10°/−15° C., the disappearance of the acid chloride carbonyl band being checked by infra red spectroscopy. The mixture was cooled to −35°/−40° C. and and there was added thereto over a period of 30 minutes a solution, precooled to −15°/−20° C., formed by 7.1 g of 7-amino-3-(1-carbonylmethyl-1,2,3,4-tetrazol-5-ylthiomethyl)-3-cephem-4-carboxylic acid in 50 ml of methylene chloride and 2.3 g of tetramethylguanidine. The mixture was stirred for 30 minutes, the temperature was allowed to rise to 0°/+5° C. and was stirred for 120 minutes. 25 ml of water were added and the pH was adjusted from 0.5 to 1, the mixture was stirred for 15 minutes and filtered, was washed with water and dried under vacuum to give the compound of the title with a 94% yield.

The disodium salt of the compound of the title was prepared with tert-butyl sodium acetoacetate, as described in Spanish patent no 497.309.

EXAMPLE 65

7-(D-alpha-amino-4-hydroxyphenylacetamido)-desacetoxycephalosporanic acid (cephadroxyl)

0.0722 g of pyridine hydrochloride (or the corresponding beta- or gamma-picoline salts or the hydrobromides thereof) was added to 11.53 g of potassium N-(1-ethoxycarbonylpropen-2-yl)-alpha-amino-4-hydroxyphenylacetate in 27 ml of methylene chloride. The mixture was cooled to −25°/−30° C. and 4.22 g of 100% pivaloyl chloride were added. The temperature was allowed to rise to −12°/−15° C. and was held for 30 minutes, the mixture was then cooled to −55°/−60° C. and 22.15 ml of dimethylacetamide and 11 ml of methylene chloride were added. From a final temperature of −30° C., the mixture was rapidly cooled to −55° C.

Thereafter a solution, precooled to −10°/−15° C., of the salt comprising 6.45 g of 7-ADCA in 52 ml of methylene chloride and 3.49 g of tetramethylguanidine was added. The addition time was 25 minutes, the funnel being washed with 4 ml of methylene chloride, which were added to the reaction mass. The mass was held at −38°/−40° C. for 8 hours and 0.47 ml of diethylamine was added to destroy the excess anhydride. The mixture was stirred for 15 minutes, was filtered and a mixture of 22.5 ml of water and 6 ml of hydrochloric acid was added, at a temperature of −15° C., pH=2. The temperature was allowed to rise to 0° C. in 5 minutes, pH=1, hydrochloric acid was added over 10 minutes to pH 0.27 and the mass was held at pH 0.2 for 20 minutes.

After decantation the mixture was washed with 2 ml of water and precipitation was provoked with N-ethylpiperidine, the pH rising to 3.47 at 20°/21° C., with 10 ml of base being consumed. An abundant precipitate was observed. 40 ml of acetonitrile were added, the pH was 3.91 and further base was added over 40 minutes, at which time the pH was 5.4–5.5 and the total consumption of base was 12.78 ml. The mixture was stirred for 2 hours at room temperature, was filtered and washed with 30 ml of acetonitrile containing 20% water and 40% acetonitrile. 10.6 g of product with a microbiological purity of 99–100% were obtained, the cephadroxyl/7-ADCA ratio being 1:1.64.

EXAMPLE 66

7-beta-2-(2-triethylaminothiazol-4-yl)-(Z)-2-methoxyiminoacetamido-3-(1,2,3-thiadiazol-5-yl)thiomethyl-3-cephem-4-carboxylic acid 2.08 g of phosphorus pentachloride were added to a solution of 4.4 g of 2-(2-triethylaminothiazol-4-yl)-(Z)-2-methoxyimino acetic acid in 70 ml of dichloromethane and 1.41 ml of triethylamine. The mixture was stirred for 15 minutes at 0°/+5° C. and was evaporated to dryness. The resulting residue was dissolved in a mixture of 50 ml of dichloromethane and 50 ml of acetone and was reevaporated. 50 ml of acetone were added to this residue and it was filtered. The filtrate was cooled and added to a solution of 2.53 g of 7-amino-3-(1,2,3-thiadiazol-5-yl)thiomethyl-3-cephem-4-carboxylic acid in 50 ml of dichloromethane with 0.88 g of tetramethylguanidine and 1.41 ml of triethylamine.

The mixture was stirred at 0°/+5° C. for 30 minutes and at 20°/22° C. for 1 hour. 75 ml of water were added, 4N HCl was added to pH 2, 100 ml of water were added, the organic phase was decanted off and the aqueous phase was extracted three times with ethyl acetate (150 ml each time). The mixture of the organic phases was washed twice with water, dried with magnesium sulphate and the solvent was evaporated to give 5.7 g of the product of the title.

EXAMPLE 67

7-amino-3-(1-methyl-1,2,3,4-tetrazol-5-yl)thiomethyl-cephalosporanic acid N-dimethyl-N″-methyl-N′,N″-propyleneguanidine salt 1.42 g of N-dimethyl-N″-methyl-N′,N″-propyleneguanidine were added to a suspension of 3.28 g of 7-amino-3-(1-methyl-1,2,3,4-tetrazol-5-yl)thiomethyl-cephalosporanic acid in a mixture of dichloromethane (15 ml) and methanol (10 ml) and a solution was obtained with stirring at room temperature.

EXAMPLE 68

Salt of 2-oxo-3-amino-4-methyl-azetidine-1-sulphonic acid 1.53 g of M-TDB were added to a suspension of 1.80 g of 2-oxo-3-amino-4-methyl-azetidine-1-sulphonic acid in 20 ml of dichloromethane and a solution of the corresponding salt was obtained. This salt was isolated by evaporation at reduced pressure. Molecular formula $C_{12}H_{23}N_5O_4S$. Molecular weight 333.38. Microanalysis: calculated: C% 43.2; H% 6.9; N% 21.0 and S% 9.6; Found: C% 43.0; H% 6.7; N% 21.3 and S% 9.8. The analysis was made without prior purification of the products, since the starting products were extremely pure: IR(KBr)$\nu$max. cm$^{-1}$: 1740 (C=0, beta-lactam); 1360 and 1150 (—SO$_3^-$).

EXAMPLE 69

Salt of 7-alpha-amino-3-[(1,2,3-thiadiazol-5-yl)thiomethyl]-3-cephem-4-carboxylic acid 1.292 g. of pentamethylguanidine were added to a suspension of 3.304 g of the acid of the title in 10 ml of dichloromethane and the corresponding salt solution was obtained by stirring at room temperature. This salt was isolated by evaporation of the solvent at reduced pressure. Molecular formula: $C_{16}H_{25}N_7O_3S_3$. Molecular weight: 459.59. Microanalysis: calculated: C% 41.8; H% 5.5; N% 21.3; S% 20.9; found: C% 41.6; H% 5.5; N% 21.5; S% 20.7. The analysis was made without prior purification since the starting acid and base were extremely pure. IR(KBr)$\nu$max. cm$^{-1}$: 1745 (C=0, beta-lactam) and 1600 (—COO$^-$).

EXAMPLE 70

Salt of 7-amino-3(paratetramethylguanidine-sulphate-2-methoxycinnamoyl-3-oxymethyl)-3-cephem-4-carboxylic acid 1.152 g of tetramethylguanidine and 1.532 g of M-TDB were added successively to a suspension of 4.865 g of 7-amino-3(parabisulphate-2-methoxycinnamoyl-3-oxymethyl)-3-cephem-4-carboxylic acid in 20 ml of dichloromethane and 10 ml of methanol and the corresponding salt was obtained. This was isolated by evaporation of the solvent at reduced pressure. Molecular formula: $C_{31}H_{46}N_8O_{10}S_2$. Molecular weight: 754.87. Microanalysis, calculated: C% 49.3; H% 6.1; N% 14.8; S% 8.5; found: C% 49.0; H% 6.0; N% 14.5; S% 8.7. The analysis was made without prior purification since the starting acid and bases were extremely pure. IR(KBr)$\nu$max. cm$^{-1}$: 1750 (C=O, beta-lactam) 1600 (—COO$^-$) 1370 and 1180 (—O—SO$_3^-$).

EXAMPLE 71

Salt of 2-oxo-3-amino-azetidine-1-phosphonic acid 1.292 g of pentamethylguanidine were added to a suspension of 1.651 g of the acid of the title in a mixture of 10 ml of dichloromethane and 5 ml of methanol, the corresponding salt being obtained by stirring. The salt was isolated by evaporation of the solvent at reduced pressure. Molecular formula: $C_9H_{22}N_5O_4P$. Molecular weight: 295.28. Microanalysis: calculated: C% 36.6; H% 7.5; N% 23.7; P% 10.5. Found: C% 36.6; H% 7.4; N% 23.5; P% 10.7. The analysis was made without prior purification since the starting products were extremely pure. IR(KBr)$\nu$max. cm$^{-1}$: 1735 (C=O, beta-lactam).

EXAMPLE 72

Salt of 7-beta-amino-7-alpha-methoxy-3-azidomethyl-3-cephem-4-carboxylic acid 1.16 g of tetramethylguanidine were added, at $+10°/+15°$ C., to a suspension of 2.85 g of the acid of the title in 20 ml of dichloromethane, to give the corresponding salt.

EXAMPLE 73

Salt of 7-beta-amino-7-alpha-methoxy-3-azidomethyl-3-cephem-4-carboxylic acid

Following Example 72, but replacing the tetramethylguanidine with 1.55 g of M-TDB a solution of the corresponding salt was also obtained.

EXAMPLE 74

Salt of 7-amino-3-methyl-3-cephem-4-carboxylic acid 1.16 g of tetramethylguanidine were added to a suspension of 2.14 g of the acid of the title in 25 ml of dichloromethane, cooled to 0°/−5° C., a solution of the corresponding salt being obtained after a few minutes stirring at 10°/15° C. The salt of the compound of the title was isolated by evaporation of the solvent at reduced pressure and suspension of the semisolid residue in ethyl ether, with filtration and drying under vacuum. The result was a very hygroscopic solid having the following characteristics: IR(KBr)$\nu$max cm$^{-1}$=1740 (C=O, beta-lactam) 1600 (—COO$^-$, wide band). $^1$H-NMR (CDCl$_3$)$\delta$ppm: 2.01

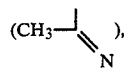

3.03 (CH$_3$-TMG) [$\alpha$]$_D^{20}$=+76.7 (C=1% DMSO); [$\alpha$]$_D^{20}$=+83.6 (C=1% H$_2$O).

EXAMPLE 75

Salt of 7-amino-3-methyl-3-cephem-4-carboxylic acid 1.40 g of TDB were added to a suspension of 2.14 g of the acid of the title in 25 ml of dichloromethane to give a solution of the corresponding salt by stirring at room temperature. The salt was isolated quantitatively by evaporation of the solvent at reduced pressure, suspension of the resulting residue in ethyl ether, filtration and drying under vacuum, to give a hygroscopic solid having m.p. 145°-155° C. (decomp.) IR(KBr)$\nu$max. cm$^{-1}$=1750 (C=O, beta-lactam) 1565 (—COO$^-$).

EXAMPLE 76

Salt of 7-amino-3-[(5-methyl-1,3,4-thiadiazol-2-yl)thiomethyl]-3-cephem-4-carboxylic acid 1.16 g of tetramethylguanidine were added to a suspension of 3.45 g of the acid of the title in 20 ml of dichloromethane. A solution of the corresponding salt was quickly obtained and was isolated by evaporation of the solvent at reduced pressure. The resulting residue was suspended in ethyl ether and filtered. The product, dried under vacuum, corresponded to the said salt and was a very hygroscopic solid. IR(KBr)$\nu$max. cm$^{-1}$: 1750 (beta-lactam, C=O) 1600 (—COO$^-$). $^1$H-NMR (CDCl$_3$)$\delta$ppm: 2.99 (CH$_3$-, tetramethylguanindine); 2.69

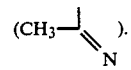

[$\alpha$]$_D^{20}$=−70.4° (C=1% DMSO); [$\alpha$]$_D^{20}$=−57.2° (C=1% H$_2$O).

EXAMPLE 77

Salt of 7-amino-3-[(5-methyl-1,3,4-thiadiazol-2-yl)thiomethyl]-3-cephem-4-carboxylic acid Following Example 76 but replacing the tetramethylguanidine by 1.54 g of M-TDB, a solution of the corresponding salt was also obtained. The salt was isolated as a hygroscopic solid under the same conditions. M.p. 35°-40° C. change of appearance; 70° (decomp.) IR(KBr)$\nu$max. cm$^{-1}$: 1755 (C=O, beta-lactam), 1595 (—COO$^-$); wide band.

EXAMPLE 78

Salt of 7-amino-3-azidomethyl-3-cephem-4-carboxylic acid 1.40 g of TDB were added to a suspension of 2.55 g of the acid of the title in 20 ml of dichloromethane to give a solution of the corresponding salt which was isolated by evaporation of the solvent at reduced pressure, giving a hygroscopic solid which was suspended in ethyl ether, was filtered and dried under vacuum at room temperature. M.p. 105°-130° C. (decomp.) IR(KBr)$\nu$max. cm$^{-1}$=1760 (C=O, beta-lactam); 2100 and 2015 (N$_3$—) and 1640 (wide band).

EXAMPLE 79

7-beta-(2-chloroacetamido)-7-alpha-methoxy-3-azidomethyl-3-cephem-4-carboxylic acid 1.16 g of tetramethylguanidine and 1.01 g of triethylamine were added successively to a suspension of 5.70 g of 7-beta-amino-7-alpha-methoxy-3-azidomethyl-3-cephem-4-carboxylic acid in 30 ml of dichloromethane. The resulting solution was cooled to −45°/−40° C. and there was added thereto over a period of 30 minutes a solution of 2.48 g of chloroacetyl chloride in 10 ml of dichloromethane. The reaction was complete in a further 60 minutes at −35°/−40° C. 15 ml of water were added and the pH was adjusted to 7.2 with ammonia at 0°/+5° C., the water phase was decanted off and was adjusted to pH 0.5 with 37.5% hydrochloric acid. The mixture was filtered and washed with water and n-hexane, to give 6.95 g of the product of the title, with a yield of 96%. IR(KBr)νmax. cm$^{-1}$=2100 (—N$_3$), 1770 (C=O, beta-lactam), 1700 (—COOH) and 1685

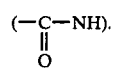

EXAMPLE 80

7-beta-(2-bromoacetamido)-7-alpha-methoxy-3-azidomethyl-3-cephem-4-carboxylic acid Following Example 79 but replacing the chloroacetyl chloride by 3.46 g of chloroacetyl bromide, 7.47 g (yield 92%) of the product of the title were obtained. IR(KBr)νmax. cm$^{-1}$: 2100 (—N$_3$), 1765 (C=O, beta-lactam), 1700 (—COOH) and 1685 (—CONH—). The pH of the solution was adjusted to 6.8.

EXAMPLE 81

7-beta-(2-chloropropionamido)-7-alpha-methoxy-3-azidomethyl-3-cephem-4-carboxylic acid Following Example 79, but replacing the chloroacetyl chloride by 2.79 g of 2-chloropropenyl chloride, 6.99 g (yield 93%) of the compound of the title were obtained. IR(KBr)νmax. cm$^{-1}$: 2100 (—N$_3$), 1765 (C=O, beta-lactam), 1700 (—COOH) and 1685 (—CONH).

EXAMPLE 82

Recovery of the acetonitrile and tetramethylguanidine from the cephalexin, cephradin and cephadroxyl precipitation liquors Powdered NaOH up to a total of 14.00 g (purity 97%) was added to the precipitation liquors with NH$_4$OH, from which the antibiotic had been washed and cooled to 0°/+5° C. The temperature was allowed to rise to 15°/20° C., with a speedy total solution and separation of phases. The phases were decanted and the acetonitrile was recovered from the organic phase (upper) by fractional distillation, with a 90–95% yield and the tetramethylguanidine with a 80–95% yield (IR=to standard and purity of 97–100% by acidimetric titration).

What we claim is:

1. Guanidine salts of amino-betalactamic acids having the formula I

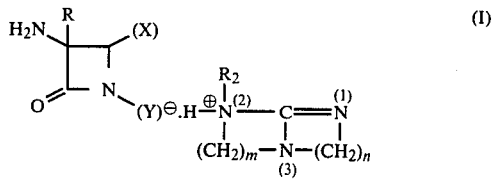

where: m=n=0 to represent in this case that the atom of N(1) supports a hydrogen or a methyl group; the atom of N(2) a methyl group and the atom of N(3) two methyl groups, forming an open chain guanidine; or m=n=3;

(Y) is a group selected from PO$_3$H and SO$_3$;

(X) is a hydrogen atom or a methyl group;

R is an atom of hydrogen or a methoxy or ethoxy group; and

R$_2$ is an atom of hydrogen or a methyl, ethyl, benzyl or phenyl group.

2. The salts of claim 1, in the formula I whereof R$_2$ is hydrogen and m=n=3, the resulting compounds having the formula II

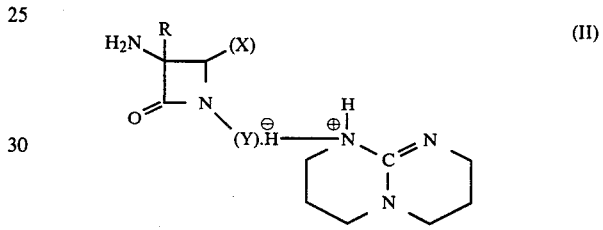

where R, (X) and (Y) are as hereinbefore defined.

3. The salts of claim 1, in the formula I whereof m=n=0, the atom of N(1) supports an atom of hydrogen, the atom of N(2) a methyl group and the atom of N(3) two methyl groups, the resulting compound having the formula III

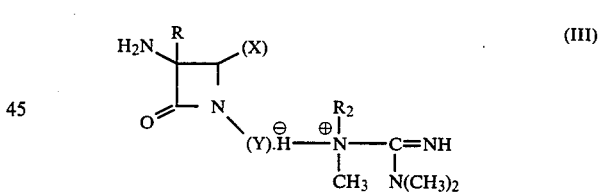

where R, R$_2$, (X) and (Y) are as hereinbefore defined.

4. The salts of claim 1, in the formula I whereof m=n=0, the atom of N(1) supports a methyl group, the atom of N(2) a methyl group and the atom of N(3) two methyl groups, the resulting compound having the formula IV

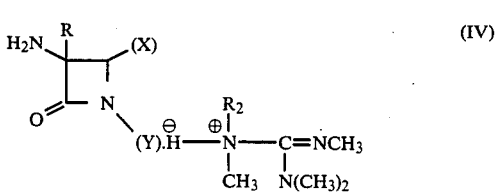

where R, R$_2$, (X) and (Y) are as hereinbefore defined.

5. The salts of claim 3, in the formula III whereof R$_2$ is a methyl group, the resulting compound having the formula V

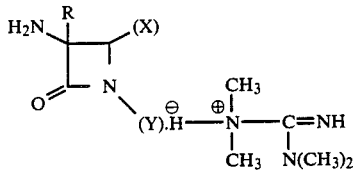

where R, (X) and (Y) are as hereinbefore defined.

6. The salts of claim 1, in the formula I whereof (X) is a methyl group, (Y) is SO$_3$, R is an atom of hydrogen, R$_2$ is a methyl group and m=n=3, the resulting compound having the formula VI

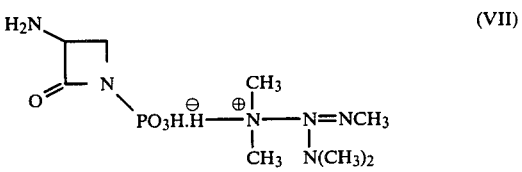

7. The salts of claim 1, in the formula I whereof R and (X) are atoms of hydrogen, (Y) is PO$_3$H, R$_2$ is a methyl group, m=m=0 and the atom of N(1) supports a methyl group, the atom of N(2) a methyl group and the atom of N(3) two methyl groups, the resulting compound having the formula VII

* * * * *

UNITED STATES PATENT AND TRADEMARK OFFICE
CERTIFICATE OF CORRECTION

PATENT NO. : 4,659,814

DATED : April 21, 1987

INVENTOR(S) : Palomo-Coll, et al.

It is certified that error appears in the above-identified patent and that said Letters Patent is hereby corrected as shown below:

Column 3, line 16, "X=-COO-" should read as -- Z=-COO⁻ --.

Column 3, line 40 " 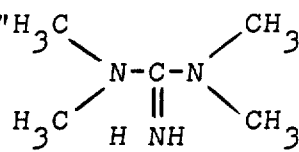 " should read as

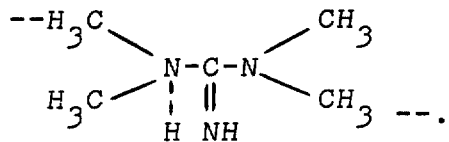 --.

Column 4, line 52, "tetramethylethyguanidine" should read as --tetramethylethylguanidine--.

UNITED STATES PATENT AND TRADEMARK OFFICE
CERTIFICATE OF CORRECTION

PATENT NO. : 4,659,814

DATED : April 21, 1987

INVENTOR(S) : Palomo-Coll, et al.

It is certified that error appears in the above-identified patent and that said Letters Patent is hereby corrected as shown below:

Column 11, line 26, "(3-methoxy-pyridazine-" should read as --(3-methoxy-pyridazin- --.

Column 14, line 14, "-3-cefem-4" should read as -- -3-cephem-4--.

Column 16, line 66, "-5-ylthiomethyl" should read as -- -5-yl-thiomethyl--.

IN THE CLAIMS:

Column 22, line 6, in Formula (I) that portion of the formula reading "(Y) $^{\ominus}$.H-" should read as --(Y) $^{\ominus}$·H- --.

Column 22, line 30, in Formula (II) that portion of the formula reading "(Y). $^{\ominus}_{H-}$ " should read as --(Y)$^{\ominus}$ · H- --.

Column 22, line 46, in Formula (III) that portion of the formula reading "(Y). $^{\ominus}_{H-}$ " should read as --(Y)$^{\ominus}$ · H- --.

Column 22, line 61, in Formula (IV) that portion of the formula reading "(Y). $^{\ominus}_{H-}$ " should read as --(Y)$^{\ominus}$ · H- --.

Column 23, line 10, in Formula (V) that portion of the formula reading "(Y). $^{\ominus}_{H-}$ " should read as --(Y)$^{\ominus}$ · H- --.

UNITED STATES PATENT AND TRADEMARK OFFICE
CERTIFICATE OF CORRECTION

PATENT NO. : 4,659,814
DATED : April 21, 1987
INVENTOR(S) : Palomo-Coll, et al.

It is certified that error appears in the above-identified patent and that said Letters Patent is hereby corrected as shown below:

Column 24, line 6, in Formula (VI) that portion of the formula reading "$SO_3 \cdot {}^{\ominus}H-$" should read as $-- SO_3{}^{\ominus} \cdot H- --$.

Column 24, line 22, in Formula (VII) that portion of the formula reading "$PO_3H \cdot {}^{\ominus}H-$" should read as "$PO_3H{}^{\ominus} \cdot H- --$.

Column 24, line 22, in Formula (VII) that portion of the formula reading "$-N=NCH_3$" should read as $$-- \begin{array}{c} -C=NCH_3 \\ | \\ N(CH_3)_2 \end{array} --$$

(should read as $\begin{array}{c} | \\ N(CH_3)_2 \end{array}$)

Column 24, line 13, "m=m=0" should read as --m=n=0--.

Signed and Sealed this

Twenty-third Day of February, 1988

Attest:

DONALD J. QUIGG

Attesting Officer            Commissioner of Patents and Trademarks